(12) United States Patent
Carlyon (10) Patent No.: US 8,506,527 B2
(45) Date of Patent: Aug. 13, 2013

(54) SYRINGE ASSEMBLY WITH PLUNGER HAVING A SECONDARY DISPENSING RESERVOIR

(75) Inventor: James L. Carlyon, Farmington, MO (US)

(73) Assignee: Covidien LP, Mansfield, MA (US)

( * ) Notice: Subject to any disclaimer, the term of this patent is extended or adjusted under 35 U.S.C. 154(b) by 20 days.

(21) Appl. No.: 13/424,607

(22) Filed: Mar. 20, 2012

(65) Prior Publication Data
US 2012/0220950 A1    Aug. 30, 2012

Related U.S. Application Data

(63) Continuation of application No. 12/482,916, filed on Jun. 11, 2009, now Pat. No. 8,142,403.

(60) Provisional application No. 61/076,841, filed on Jun. 30, 2008.

(51) Int. Cl.
*A61M 5/00* (2006.01)

(52) U.S. Cl.
USPC ............................................. 604/91; 604/231

(58) Field of Classification Search
USPC ..................................................... 604/82–92
See application file for complete search history.

(56) References Cited

U.S. PATENT DOCUMENTS

| | | |
|---|---|---|
| 4,391,273 A | 7/1983 | Chiquiar-Arias |
| 4,439,184 A | 3/1984 | Wheeler |
| 4,715,854 A | 12/1987 | Vaillancourt |
| 4,929,230 A | 5/1990 | Pfleger |
| 5,298,024 A | 3/1994 | Richmond |
| 5,476,449 A * | 12/1995 | Richmond ............ 604/87 |
| 5,501,673 A | 3/1996 | Hjertman et al. |
| 5,599,312 A | 2/1997 | Higashikawa |
| 5,637,087 A | 6/1997 | O'Neil et al. |
| 5,685,846 A | 11/1997 | Michaels |
| 5,697,915 A | 12/1997 | Lynn |
| 5,704,918 A | 1/1998 | Higashikawa |
| 5,716,338 A | 2/1998 | Hjertman et al. |
| 5,720,731 A | 2/1998 | Aramata et al. |
| 5,743,879 A | 4/1998 | Kriesel |
| 5,788,670 A | 8/1998 | Reinhard et al. |
| 5,830,193 A | 11/1998 | Higashikawa |
| 6,053,894 A | 4/2000 | Shadd |
| 6,348,043 B1 | 2/2002 | Hagen et al. |
| 6,740,062 B2 | 5/2004 | Hjertman |
| 6,866,653 B2 | 3/2005 | Bae |
| 7,033,337 B2 | 4/2006 | Hjertman |
| 7,077,827 B2 | 7/2006 | Greenfield |
| 7,104,971 B2 | 9/2006 | Hjertman |
| 2002/0035351 A1 | 3/2002 | Lodice |

(Continued)

*Primary Examiner* — Kevin C Sirmons
*Assistant Examiner* — Brandy S Lee
(74) *Attorney, Agent, or Firm* — Lisa E. Winsor, Esq.

(57) ABSTRACT

A method of supplying a flush/lock solution to a catheter assembly is disclosed which includes the steps of securing a distal end of a syringe assembly to the catheter assembly, advancing a plunger rod of the syringe assembly within a body of the syringe assembly until the plunger bottoms out on a distal wall of the body to eject a first fluid from a first fluid reservoir of the body from the fluid outlet of the syringe assembly, and after the plunger bottoms out on the distal wall of the body, advancing the plunger rod further within the body to advance a piercing member to pierce the plunger to eject a second fluid from a second fluid reservoir defined by the plunger from the fluid outlet.

6 Claims, 6 Drawing Sheets

(56) References Cited

U.S. PATENT DOCUMENTS

| | | |
|---|---|---|
| 2002/0087122 A1 | 7/2002 | Sogaro |
| 2002/0099384 A1 | 7/2002 | Scribner et al. |
| 2002/0138043 A1 | 9/2002 | Tanaka et al. |
| 2003/0105433 A1 | 6/2003 | Ruben |
| 2003/0199816 A1 | 10/2003 | Ramming |
| 2004/0044316 A1 | 3/2004 | Greenfield |
| 2004/0097875 A1 | 5/2004 | Bae |
| 2004/0116871 A1 | 6/2004 | Vincent |
| 2004/0185028 A1* | 9/2004 | Hu et al. .................. 424/78.27 |
| 2005/0171506 A1 | 8/2005 | Hallahan et al. |
| 2005/0240157 A1 | 10/2005 | Amisar et al. |
| 2005/0245880 A1 | 11/2005 | Howlett et al. |
| 2009/0165789 A1 | 7/2009 | Kobayashi et al. |

\* cited by examiner

SYRINGE ASSEMBLY WITH PLUNGER HAVING A SECONDARY DISPENSING RESERVOIR

CROSS-REFERENCE TO RELATED APPLICATIONS

This application is a continuation of application Ser. No. 12/482,916, filed Jun. 11, 2009, which claims priority from U.S. provisional application Ser. No. 61/076,841, filed Jun. 30, 2008, the entirety of each of which is incorporated herein by reference.

BACKGROUND

1. Technical Field

The present disclosure relates to syringes and, more particularly, to a syringe having a primary reservoir and a secondary reservoir for injecting a secondary solution subsequent to injection of a primary solution from the primary reservoir. The present disclosure also relates to a method of supplying a flush/lock solution and an antimicrobial solution to a catheter assembly using a single syringe.

2. Background of Related Art

Intravenous or I.V. catheters which are inserted into a patient's vasculature, e.g., vein, to facilitate a variety of different medical procedures, including blood withdrawal, medication delivery, dialysis, etc., over an extended period of time are well known in the art. Such I.V. catheters minimize the pain and discomfort to a patient associated with multiple needle injections which may be required during a hospital stay.

Syringe assemblies are commonly used to inject fluids, e.g., medication, into an I.V. catheter. Typically, after a medication has been injected from a syringe assembly into the I.V. catheter, a flush solution is injected into the I.V. catheter to force any medication remaining in the catheter into the patient.

One problem currently associated with the use of a syringe assembly to inject fluid into an I.V. catheter is that attachment of the syringe assembly to the I.V. catheter may introduce contaminants into the I.V. catheter or the reusable valve structure of the catheter, which may lead to infection in the patient.

It is known to inject an anti-microbial solution into an indwelling catheter to guard against infection. However, the injection of an anti-microbial solution into I.V. catheter requires the attachment of a second syringe to the I.V. catheter which further increases the risk of infection to the patient.

Accordingly, a continuing need exists in the medical arts for a syringe assembly which can function to flush an I.V. catheter assembly while minimizing the risk of infection to a patient.

SUMMARY

A syringe assembly is disclosed which includes a syringe body defining a first fluid reservoir and a fluid outlet. A plunger assembly includes a plunger rod and a plunger. The plunger is supported on a distal end of the plunger rod and defines a second fluid reservoir. The plunger is movable within the syringe body from a retracted position to an advanced position to eject fluid from the first fluid reservoir. A piercing member is supported on a distal end of the plunger rod within the second fluid reservoir. The piercing member is movable to pierce the plunger to eject fluid from the second fluid reservoir when a predetermined force is applied to the plunger in the advanced position. In one embodiment, the plunger includes at least one external annular groove adjacent an outwardly bowed internal wall and is collapsible upon application of the predetermined force to the plunger. It is also envisioned that the plunger may be constructed of more than one material or component to provide for axial stiffness but allow for collapsing or "folding" at the predetermined force due to fluid pressure acting upon the internal wall.

The plunger can include a plurality of external annular grooves or have a bellows-like construction.

In one embodiment, the piercing member includes a piercing tip. The piercing member can include at least one external groove, wherein fluid in the second fluid reservoir flows along the at least one external groove to the fluid outlet. The at least one external groove can include a plurality of external grooves.

In one embodiment, the first fluid reservoir contains a first fluid and the second fluid reservoir contains a second fluid which is different from the first fluid. The first fluid can be a flush solution and the second fluid can be an anti-microbial solution.

In one embodiment, the plunger rod includes a circular disc secured to the plunger and the circular disc includes a frangible portion. The frangible portion defines a centrally located secondary plunger which is dimensioned to move within the second fluid reservoir to eject fluid from the second fluid reservoir. The piercing member can extend distally from a distal surface of the secondary plunger. The frangible portion is constructed to break upon application of the predetermined force to the plunger. The predetermined force should be greater than the force required to initiate movement of the plunger.

A method of supplying a flush/lock solution to a catheter assembly is disclosed which includes the steps of providing a syringe assembly including a body defining a first fluid reservoir containing a first fluid and a fluid outlet, a plunger assembly including a plunger rod and a plunger defining a second fluid reservoir containing a second fluid, and a piercing member for piercing the plunger; securing a distal end of the syringe assembly to the catheter assembly; advancing the plunger rod within the body until the plunger bottoms out on a distal wall of the body to eject the first fluid in the first fluid reservoir from the fluid outlet; and after the plunger bottoms out on the distal wall of the body, advancing the plunger rod further within the body to advance the piercing member to pierce the plunger to eject the second fluid in the second fluid reservoir from the fluid outlet.

In one embodiment, the first fluid is a flush/lock solution such as saline, and the second solution is an anti-microbial solution such as polyhexamethylenebiguanide (PHMB).

BRIEF DESCRIPTION OF THE DRAWINGS

Various embodiments of the presently disclosed syringe assembly with a plunger having a secondary dispensing reservoir are disclosed herein with reference to the drawings, wherein.

DETAILED DESCRIPTION OF EMBODIMENTS

Embodiments of the presently disclosed syringe assembly with a plunger having a secondary dispensing reservoir will now be described in detail with reference to the drawings wherein like reference numerals designate identical or corresponding elements in each of the several views. In this description, the term proximal is generally used to indicate the relative nearness of a referenced item to a user of the device and the term distal is used to indicate the relative remoteness of a referenced item to a user of the device.

Figure 1:
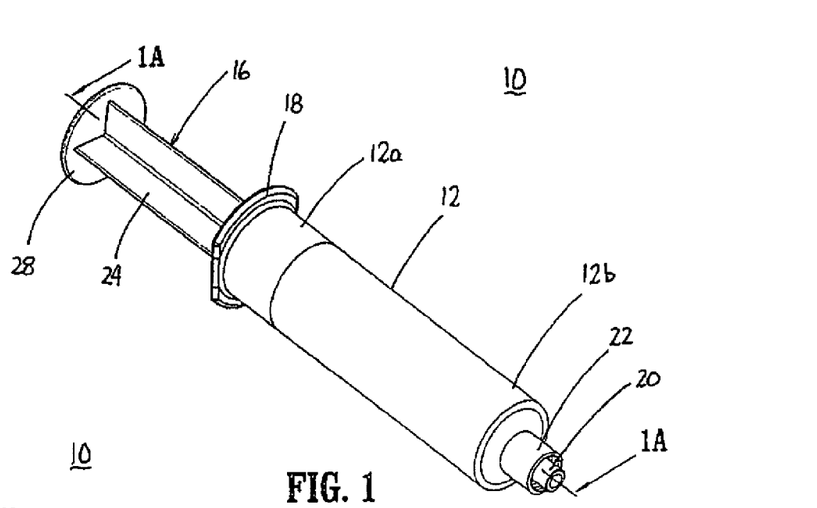
FIG. 1 is a side perspective view from the distal end of one embodiment of the presently disclosed syringe assembly with a plunger having a secondary dispensing reservoir.
Figure 1A:
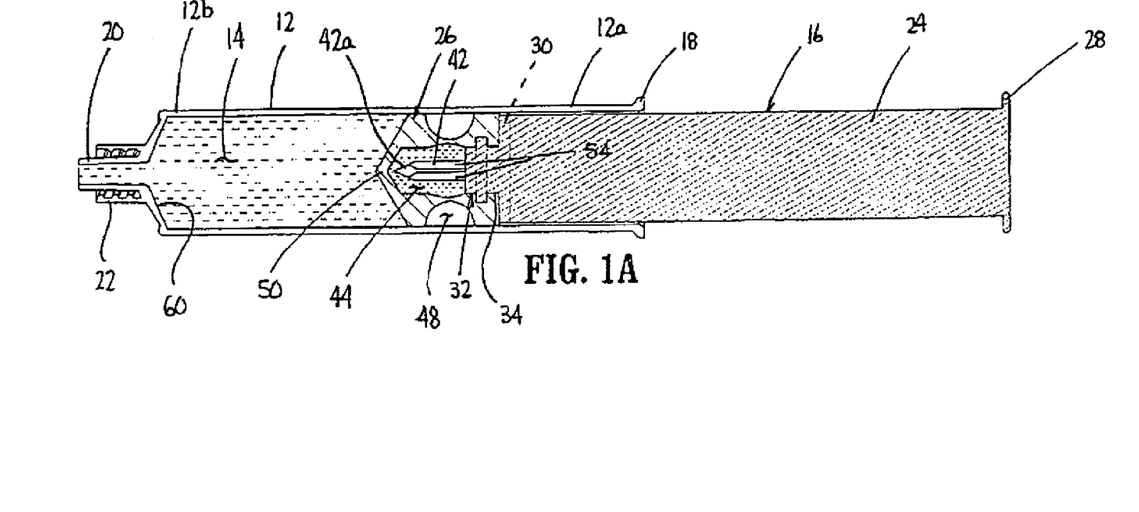
FIG. 1A is a side cross-sectional view of the syringe assembly shown in FIG. 1 taken along section lines 1A-1A of FIG. 1 with the syringe plunger in a retracted position.
Figure 2:
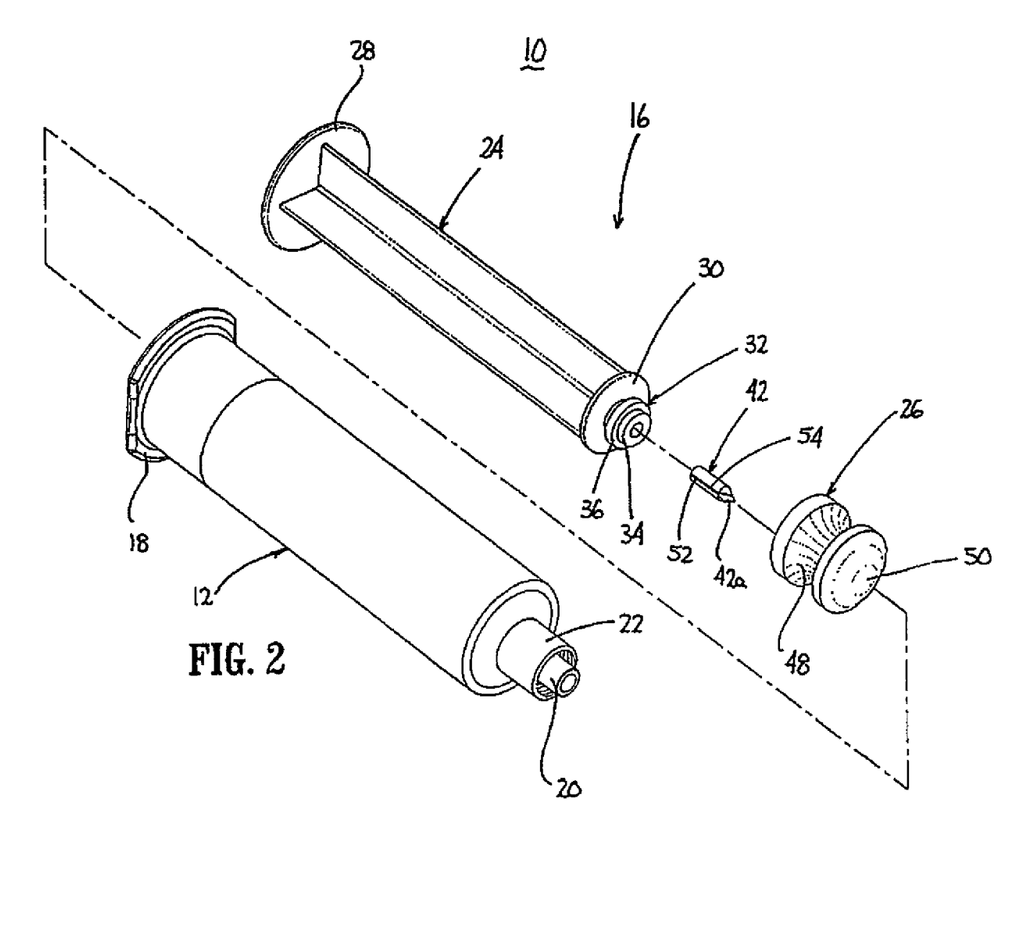
FIG. 2 is a side perspective exploded view from the distal end of the syringe assembly shown in FIG. 1.
Figure 3:
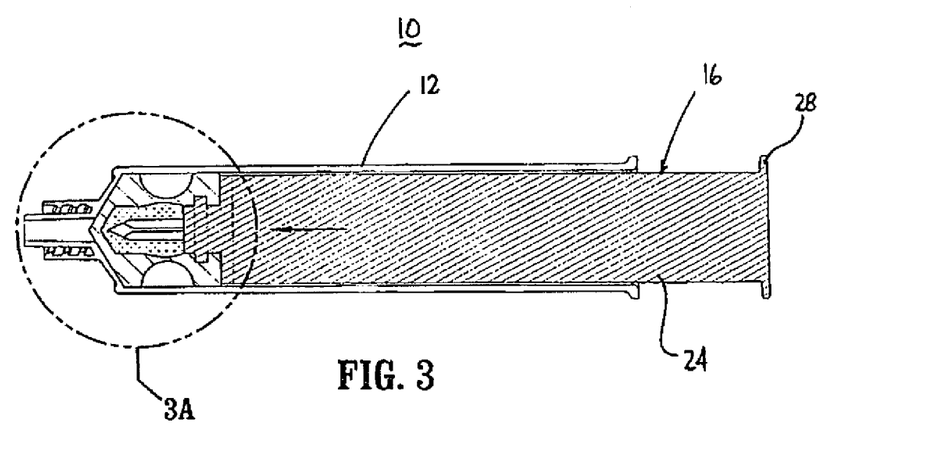
FIG. 3 is a side cross-sectional view of the syringe assembly shown in FIG. 1A with the syringe plunger in an advanced position.

FIGS. 1-3 illustrate one embodiment of the presently disclosed syringe assembly with a plunger having a secondary dispensing reservoir shown generally as 10. Briefly, syringe assembly 10 includes a syringe body 12 defining a primary fluid reservoir 14 and a plunger assembly 16. Syringe body 12 has a proximal open end 12a having a gripping flange 18 and a distal end 12b defining a conical or tapered fluid outlet 20. A luer-type connector or similar connecting structure 22 is positioned about fluid outlet 20. Connecting structure 22 is configured to releasably engage connecting structure on a medical device (not shown), e.g., an indwelling catheter, to releasably secure syringe assembly 10 to the medical device.

Plunger assembly 16 includes a plunger rod 24 and a plunger 26 (FIG. 1A). The proximal end of plunger rod 24 includes a finger engagement member 28 and the distal end of plunger rod 24 includes a circular disc 30 (FIG. 2). Plunger rod 24 has a +-shaped body which interconnects finger engagement member 28 and circular disc 30. A stepped extension 32 is formed on a distal face of disc 30. Extension 32 includes a cylindrical body 34 and a step 36. As illustrated in FIG. 1A, step 36 is received within a stepped recess 38 formed within plunger 26 to secure plunger 26 onto the distal end of plunger rod 24. The distal face of extension 32 has a longitudinal bore 40 (FIG. 2) which is dimensioned to receive a piercing tip 42 which will be discussed in further detail below.

Referring to FIGS. 1A and 2, plunger 26 is formed of a resilient material, e.g., rubber, and defines a secondary fluid reservoir 44 (FIG. 1A). The outer surface of plunger 26 is dimensioned to sealingly engage an internal surface 46 of syringe body 12. An annular recess 48 is defined about plunger 26. Annular recess 48 is provided to allow plunger 26 to collapse after a predetermined axial force is applied to plunger 26 as will be discussed in further detail below. The distal end of plunger 26 includes a piercable area 50 of reduced thickness.

Plunger 26 also includes an internal wall 48a which bows outwardly and is aligned with annular recess 48. Internal wall 48a expands outwardly as piercable tip 42 advances towards piercable area 50 of plunger 26 to increase the width of secondary fluid reservoir 44 and compensate for the reduced length of reservoir 44. It is noted that since fluids would not be compressible within reservoir 44, the width of reservoir 44 must increase as plunger 26 is compressed to accommodate a fixed volume of fluid.

Piercing tip 42 has a proximal end 52 (FIG. 2) which is fixedly secured within bore 40 of extension 32 of plunger rod 24 and a sharpened distal end 42a. Alternatively, piercing tip 42 is formed integrally with extension 32. An external surface of piercing tip 42 defines one or more longitudinal grooves 54 (FIG. 1A), e.g., four. Piercing tip 42 is positioned within secondary fluid reservoir 44 of plunger 26 such that distal end 42a of piercing tip 42 is positioned adjacent piercable area 50 of plunger 26.

Figure 3A:
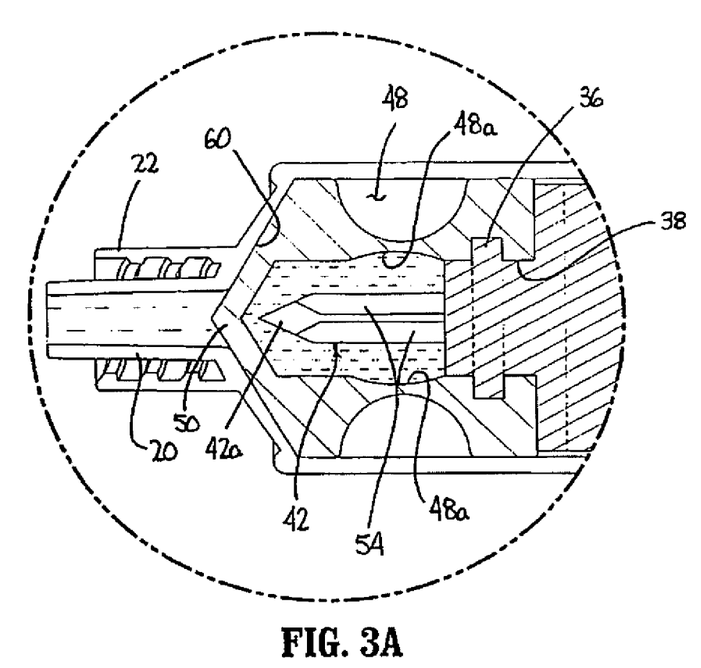
FIG. 3A is an enlarged view of the indicated area of detail shown in FIG. 3.

Referring to FIGS. 3 and 3A, when plunger assembly 16 is advanced from a retracted position (FIG. 1A) to an advanced position (FIG. 3), plunger 26 forces fluid from primary reservoir 14 through fluid outlet 20 until plunger 26 bottoms out on a distal wall 60 of syringe body 12. When plunger 26 bottoms out on distal wall 60, a further application of a predetermined force on plunger 26 transmitted through plunger rod 24 causes internal wall 48a of plunger 26 to bow outwardly such that plunger 26 can collapse. It should be noted that the predetermined force required to effect collapse of plunger 26 in combination with the force required to pierce piercable area 50 of plunger 26 must be greater than the force required to initiate movement of plunger 26 and the force required to eject fluid from primary reservoir 14.

Figure 4:
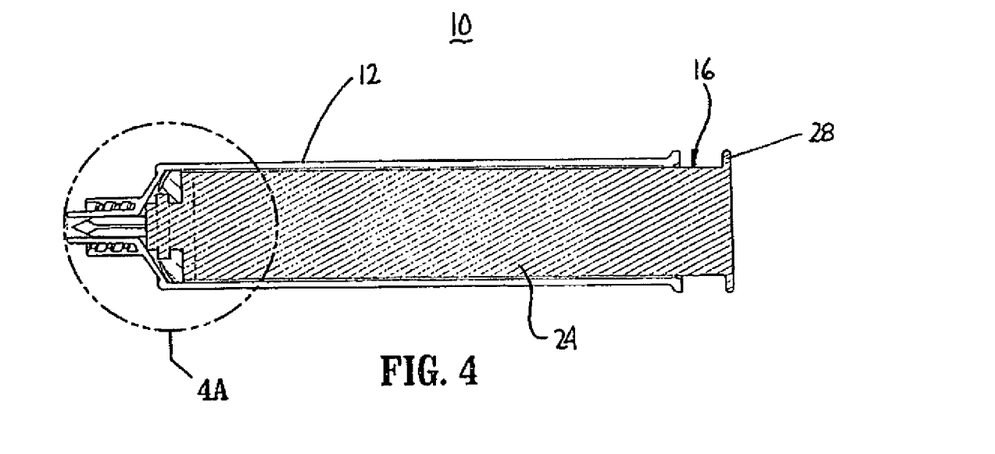
FIG. 4 is a side cross-sectional view of the syringe assembly shown in FIG. 3 with the syringe plunger in an advanced and collapsed position.
Figure 4A:
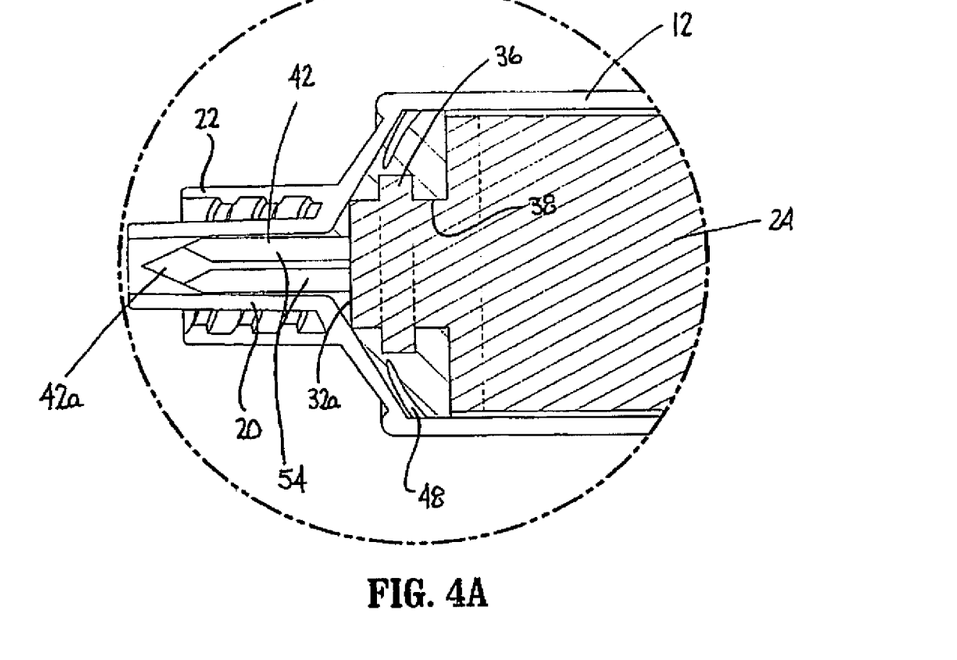
FIG. 4A is an enlarged view of the indicated area of detail shown in FIG. 4.

Referring to FIGS. 4 and 4A, when the predetermined force required to collapse plunger 26 is applied to plunger 26, plunger 26 collapses causing sharpened distal end 42a of piercing tip 40 to pierce piercable area 50 of plunger 26. As plunger 26 collapses, fluid from within secondary fluid reservoir 44 is forced to flow through grooves 54 of piercing tip 42 and through fluid outlet 20. As this occurs, the distal face 32a of extension 32 of plunger rod 24 functions as a secondary plunger to eject fluid from secondary fluid reservoir 44. It is noted that a vent (not shown) may be provided through or around a proximal end of plunger 26 to vent annular recess 46 as plunger 26 collapses.

Syringe assembly 10 is suitable for use with an indwelling catheter assembly (not shown). More specifically, in one presently disclosed method of use, syringe assembly 10 is provided with a flush or lock solution, e.g., saline, in primary reservoir 14 and an anti-microbial solution, e.g., Poly(hexamethylenebiguanide) (PHMB), in the secondary fluid reservoir 44. Syringe assembly 10 is secured to an indwelling catheter assembly (not shown) to flush the catheter assembly. After the flush/lock solution has been injected into the catheter assembly from the primary reservoir 14, the anti-microbial solution is injected into the catheter assembly. In one embodiment, the anti-microbial solution has a viscosity which is greater than that of the flush/lock solution such that the anti-microbial solution will tend to reside within reusable valve structure of the indwelling catheter (not shown). The injection of an anti-microbial solution into the reusable valve structure of an indwelling catheter minimizes the risk of patient infection caused by sources originating from the valve structure of the indwelling catheter. The presently disclosed syringe assembly facilitates the sequential injection of a flush/lock solution and anti-microbial solution into an indwelling catheter using a single syringe to further minimize the risk of infection to the patient.

In an alternative method of use, the primary reservoir may store a first fluid which mixes with a second fluid stored in the secondary fluid reservoir to provide enhanced anti-microbial activity in the reusable valve structure of an indwelling catheter. For example, the primary reservoir may store EDTA and the secondary fluid reservoir may store hydrogen peroxide. When the EDTA mixes with the hydrogen peroxide within the valve structure of the indwelling catheter, enhanced anti-microbial activity is effected.

It is also contemplated that the reusable valve structure of the indwelling catheter may be coated or impregnated with silver or silver particles and the secondary fluid reservoir may include a fluid, e.g., EDTA, which interacts with the silver or silver particles to enhance anti-microbial activity within the reusable valve structure of the indwelling catheter.

Figure 5:
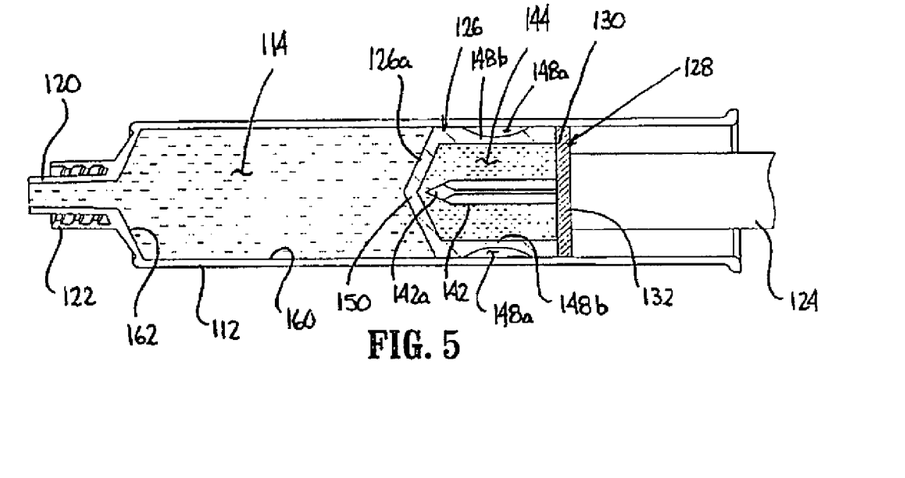
FIG. 5 is a side cross-sectional view of another embodiment of the presently disclosed syringe assembly with a plunger having a secondary dispensing reservoir and the plunger in a retracted position.
Figure 5A:
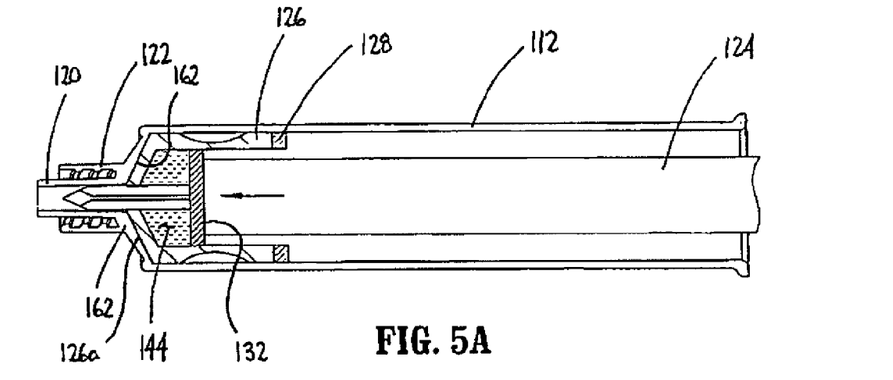
FIG. 5A is a side cross-sectional view of the syringe assembly shown in FIG. 5 with the plunger in an advanced position and the secondary plunger partially advanced through the secondary reservoir.

FIGS. 5 and 5A illustrate another embodiment of the presently disclosed syringe assembly shown as 100. Syringe assembly 100 includes a syringe body 112 defining a primary fluid reservoir 114 and a plunger assembly 116. Syringe body 112 has a proximal open end 112a and a distal end 112b defining a tapered fluid outlet 120. A luer-type connector 122 or the like is positioned about fluid outlet 120.

Plunger assembly 116 includes a plunger rod 124 and a plunger 126. Plunger rod 124 includes a circular disc 128 which is secured to a proximal surface of plunger 126 such as by adhesives. Circular disc 128 includes a circular frangible portion 130 which defines an inner secondary plunger 132 on circular disc 128. A piercing tip 142 is secured to or formed integrally with secondary plunger 132. Piercing tip 142 extends distally from secondary plunger 132 and has a tip 142a which is positioned adjacent a piercable portion 150 of plunger 126. Piercing tip 142 defines one or more grooves 154 which will be discussed in further detail below.

Plunger 126 defines a secondary fluid reservoir 144 and includes an outer surface which sealingly engages an inner wall 160 of syringe body 112 at its proximal and distal ends. A central portion of plunger 26 includes a concavity 148a defining a thinned side wall portion 148b of plunger 126. The proximal end of reservoir 144 is sealed by secondary plunger 132. When plunger assembly 116 is advanced from a retracted position (FIG. 5) to an advanced position such that a distal face 126a of plunger 126 engages a distal wall 162 of syringe body 112, further application of a predetermined force on plunger assembly 116 causes frangible portion 130 to break. When frangible portion 130 breaks, secondary plunger 132 separates from the remaining portion of circular disc 128 and begins to move through secondary fluid reservoir 144. During initial advancement of secondary plunger 132, thinned side wall portion 148b bows outwardly to compensate for the reduction in length of secondary fluid reservoir 144 and accommodate the fixed volume of fluid stored within reservoir 144. When piercing tip 142 pierces plunger 126, fluid is ejected from reservoir 144 through fluid outlet 120. As discussed above with respect to syringe assembly 10, the predetermined force required to effect separation of secondary plunger 132 from circular disc 128 must be greater than the force required to initiate movement of plunger assembly 16. It is noted that a portion of the outer periphery of secondary plunger 132 can be provided with a sealing element, e.g., an O-ring, to enhance sealing engagement of secondary plunger 132 within inner wall defining reservoir 144. It is also noted that a vent (not shown) can be provided through or around a proximal end of plunger 126 to facilitate outward movement of thinned side wall portion 148b.

Figure 6:
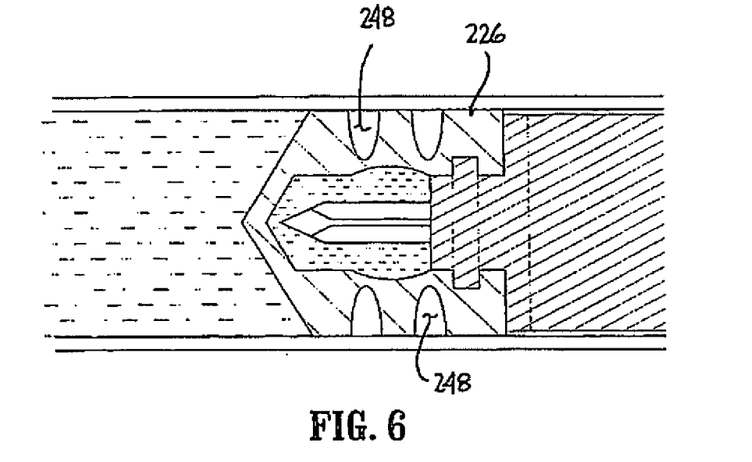
FIG. 6 is a side cross-sectional view of an alternative embodiment of the presently disclosed syringe assembly plunger.
Figure 6A:
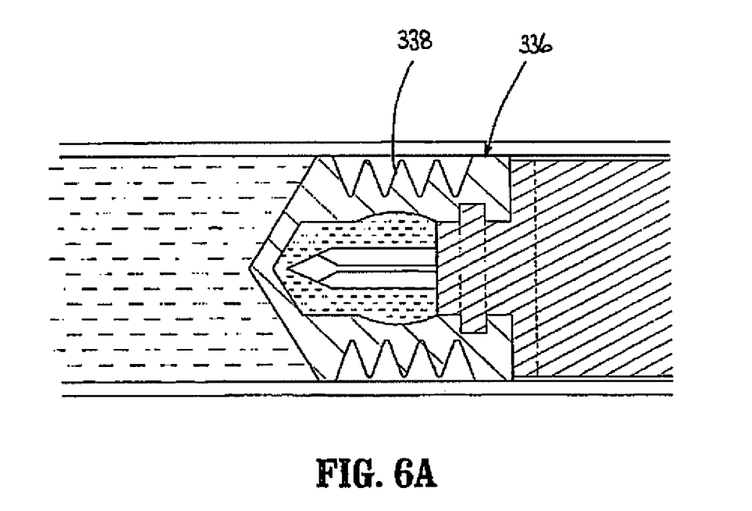
FIG. 6A is a side cross-sectional view of yet another embodiment of the presently disclosed syringe plunger.

FIGS. 6 and 6A illustrate alternative embodiments of plunger 26. In FIG. 6, plunger 226 defines a pair of annular recesses 248, as compared to a single annular recess 48 defined in plunger 26 (FIG. 1A). In FIG. 6A, plunger 336 defines an intermediate bellows type configuration 338. Each of the plunger configurations shown in FIGS. 6 and 6A provide alternative structure for facilitating collapse of plunger. It is envisioned that a variety of different configurations could be used to achieve this result. It is further envisioned that the plunger need not collapse but rather may include other structure, such as that shown in FIGS. 5 and 5A, to dispense fluid from the secondary reservoir.

It will be understood that various modifications may be made to the embodiments disclosed herein. For example, it is envisioned that the plunger may be constructed of more than one material or component to allow for axial stiffness but also allow for collapsing or folding upon application of a predetermined force. Therefore, the above description should not be construed as limiting, but merely as exemplifications of preferred embodiments. Those skilled in the art will envision other modifications within the scope and spirit of the claims appended hereto.

What is claimed is:

1. A method of supplying a flush/lock solution to a catheter assembly comprising the following steps:
   providing a syringe assembly including a body defining a first fluid reservoir and a fluid outlet, the first fluid reservoir containing a first fluid, a plunger assembly including a plunger rod and a plunger, a second fluid reservoir defined within the plunger containing a second fluid, and a piercing member positioned within the second fluid reservoir for piercing the plunger, the piercing member being supported on a distal end of the plunger rod;
   securing a distal end of the syringe assembly to the catheter assembly;
   advancing the plunger rod within the body until the plunger bottoms out on a distal wall of the body to eject the first fluid in the first fluid reservoir from the fluid outlet; and
   after the plunger bottoms out on the distal wall of the body, advancing the plunger rod further within the body to advance the piercing member to pierce the plunger to eject the second fluid in the second fluid reservoir from the fluid outlet.

2. The method of claim 1, wherein the first fluid is a flush/lock solution and the second fluid is an anti-microbial solution.

3. The method of claim 2, wherein the flush/lock solution is saline.

4. The method of claim 3, wherein the anti-microbial solution is a polyhexamethylenebiguanide (PHMB).

5. The method of claim 2 further including the step of selecting the anti-microbial solution to have a higher viscosity than the flush/lock solution.

6. The method of claim 1, wherein the step of providing a syringe assembly includes providing a plunger rod having a disc secured to a proximal surface of the plunger, the disc having an inner frangible portion which defines a secondary plunger which is movable through the second fluid reservoir.

* * * * *